United States Patent [19]

Dikstein

[11] Patent Number: 5,376,365
[45] Date of Patent: Dec. 27, 1994

[54] METHOD OF THE TREATMENT OF DRY NOSE SYNDROME

[75] Inventor: Shabtay Dikstein, Jerusalem, Israel

[73] Assignee: Resdevco Research & Development Company Ltd., Jerusalem, Israel

[21] Appl. No.: 19,435

[22] Filed: Feb. 18, 1993

[30] Foreign Application Priority Data

Feb. 24, 1992 [IL] Israel ........................... 101056

[51] Int. Cl.$^5$ ................. A61K 31/74; A61K 31/715; A61K 31/045
[52] U.S. Cl. ......................... 424/78.02; 514/54; 514/738
[58] Field of Search ............... 424/78.37, 78.31, 78.03, 424/78.02; 514/738, 54

[56] References Cited

U.S. PATENT DOCUMENTS 5,036,095 7/1991 Andermann ................. 514/389
5,106,615 4/1992 Dikstein ..................... 424/78.04

OTHER PUBLICATIONS

Merck Manual pp. 1964–1965, 1982 (14th edition) Published by Merck & Co., Inc.
*Remington's Pharmaceutical Sciences*, Mack Publishing Co, pp. 1297, 1505, 1305, (1985).
*Merck Manual*, Merck Sharp & Dohne Res. Laboratories, pp. 2063–2065, 14th edition (1982).

*Primary Examiner*—Raymond J. Henley, III
*Attorney, Agent, or Firm*—Browdy and Neimark

[57] ABSTRACT

There are provided pharmaceutical compositions for intranasal application for the alleviation of nasal discomforts, like "dry nose syndrome" and for the treatment of a variety of diseases. These are based on the combination of an isotonic humectant solution and a high molecular weight polymer which provides the required viscosity. Preferred compositions have a non-Newtonian viscosity profile. The composition can contain one or more pharmaceutically active ingredient.

5 Claims, 1 Drawing Sheet

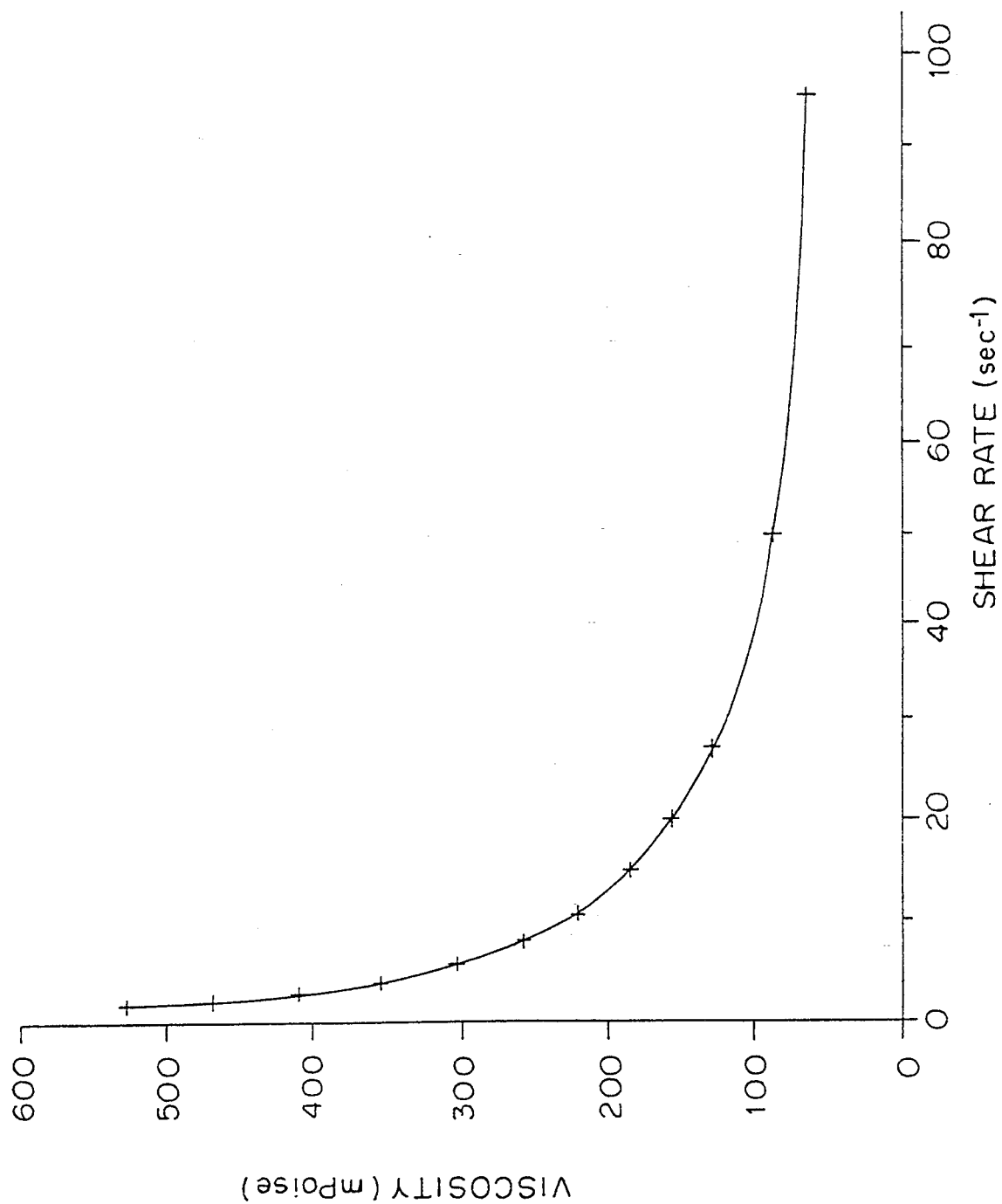

METHOD OF THE TREATMENT OF DRY NOSE SYNDROME

FIELD OF INVENTION

The "Dry Nose Syndrome", one manifestation of which is Rhinitis sicca and another is Atrophic Rhinitis, is a serious medical problem and it is possibly also a side effect of certain nose medications. The present invention overcomes the problem of "Dry Nose" by providing formulation containing a moisturizer-humectant, e.g. a polyol such as glycerine or polyalkylene glycol in a viscous base, preferably with non-newtonian rheological profile. The formulation also serves as a vehicle for drug delivery.

BACKGROUND OF INVENTION

The present treatment of abnormal state of the nose is by the use of medicated liquids or ointments administered to the nasopharynx. One of the results of administering aqueous viscous preparations is that after evaporation of the water, an unpleasant crust is formed from the viscosity-forming agent. Moreover, a very serious side effect or problem is the feeling of "Dry Nose", for which at present there does not exist a significant satisfactory treatment.

SUMMARY OF THE INVENTION

The compositions of the present invention overcome to a large extent the above delineated problems, by providing a non-newtonian gel-forming agent in the presence of a strong moisturizer such as glycerine, polyethylene glycol 300 to 1000, or polypropylene glycol of about 300 to 1000.

BRIEF DESCRIPTION OF DRAWING

The sole FIGURE is a graph of shear rate vs. viscosity of a composition according to the present invention.

DETAILED DESCRIPTION OF EMBODIMENTS

The non-newtonain gel is advantageously formed from a neutralized anionic polymer such as carbomer or hyaluronic acid. It was found unexpectedly that one needs a high viscosity so as to obtain a satisfactory clinical effect: i.e. the viscosity of Carbopol 940 at 0.3%, pH 7.0, in water. A non-newtonian gel from the practical viewpoint is one whose initial viscosity of between 1 sec to 100 sec changes at least 2-fold, and preferably at least 5-fold (See FIG. 1, Example 1).

The following Examples are intended to illustrate the present invention, without being construed in a limitative manner. In all the examples per cent is by weight.

EXAMPLE 1

| | |
|---|---|
| Carbomer 940 neutralized by NaOH | 0.4% |
| Glycerine | 2.6% |
| Water | to 100.0% |

EXAMPLE 2

| | |
|---|---|
| Carbomer 934 neutralized by NaOH | 0.6% |
| Glycerine | 2.7% |
| Water | to 100.0% |

EXAMPLE 3

| | |
|---|---|
| Carbomer 940 neutralized by NaOH | 0.5% |
| Polyethylene glycol 400 | 12.0% |
| Water | to 100.0% |

EXAMPLE 4

As example 1, with the addition of naphazoline 0.04% or other suitable decongestant.

EXAMPLE 5

As example 1, with the addition of phenylephrine 0.2% or other suitable decongestant.

EXAMPLE 6

As example 2, with the addition of dexamethasone sodium phosphate 0.05%, or other suitable antiinflammatory agent.

EXAMPLE 7

As example 1, with the addition of 0.1% diphenhydramine or other suitable antihistamine.

EXAMPLE 8

As example 2, with the addition of 0.1% neomycine.

EXAMPLE 9

As example 2, with the addition of 0.3% dihydroergotamine.

Suitable preservatives and other additives can be added to the above examples. They can be packaged in unit doses or as a spray. In all the examples the carbomer is replaceable totally or in part by hyaluronic acid. If used alone, it is used at about 1.0% concentration, provided the molecular weight is about 2 million.

In all the examples the anionic polymer can be neutralised with any physiologically acceptable inorganic or organic base.

To the viscoelastic-humectant base one can add any non-ionic drug or cationic drug in the form of a polyanion salt. Anionic drugs can be added only in low concentration (usually less than 0.05%) or as a water insoluble phase, e.g. suspension, coated particle or emulsion. Of course more than one kind of drug can be added to the final preparation. The drug included is either for local or for systemic treatment.

CLINICAL STUDIES

A preliminary study using Example 1 formulation, but only 0.1% Carbomer 940 on 10 patients, produced the following results: patients complained of burning sensation, 5 complained about unpleasant swallowing, 5 patients complained of smelling impairment. The moisturizing effect lasted up to 1 hour. Clinical studies using the preparation of example 1 on 10 patients showed that it alleviates the symptoms of "Dry Nose" feeling for about 2 hours. The beneficial action of isotonic saline in the same pathological conditions lasts for about 15 minutes only. None of the patients complained of a burning sensation, unpleasant swallowing or smelling impairment.

In another series of study we compared Example 2 with a commercial xylometazolin preparation on 5 patients suffering from dry nose syndrome during 1 week, 3 times a day. They used a composition of Example 2 for 1 week, than the commercial xylometazoline for 1 week. All patients prefered Example 2; 3 patients claimed that Example 2 has a longer and more pronounced effect.

I claim:

1. A method for the treatment or alleviation of dry nose syndrome in a patient in need thereof, comprising applying a pharmaceutically effective amount of a pharmaceutical composition to the interior of the nose of said patient said pharmaceutical composition consisting essentially of a high-viscosity isotonic mixture, in gel form having non-Newtonian rheological properties, of an humectant in the form of an isotonic amount of glycerine or a polyalkylene glycol, and 0.2–1.0 weight % of a physiologically acceptable anionic polymer having molecular weight of 500,00 to 5 million, said composition containing less than 1.5 mM of any inorganic salt.

2. A method for the treatment or alleviation of dry nose syndrome in a patient in need thereof, comprising applying to the interior of the nose of said patient, a pharmaceutical isotonic composition in the form of a gel having non-Newtonian theological properties, which comprises an isotonic concentration of a humectant and 0.2 to 1.0 wt % of a physiologically acceptable at least partially neutralized anionic polymer of a molecular weight of about 500,000 to 5,000,000 and selected from the group consisting of polyacrylates, hyaluronic acid and mixtures thereof, said composition being substantially free of any inorganic salt.

3. A method according to claim 2, where the molecular weight of the polymer is between 1,000,000 and 5,000,000.

4. A method according to claim 2, where the humectant is in the form of an isotonic solution of glycerine or of a polyalkylene glycol of a molecular weight from 300 to 1,000.

5. A method according to claim 2, which contains as further ingredient one or more of the following: a decongestant, an antiinflammatory agent, an antihistamine, an antiallergic, an antibiotic, and any other pharmaceutical agent for local or systemic action.

* * * * *